(12) United States Patent
Sealfon et al.

(10) Patent No.: US 10,576,199 B2
(45) Date of Patent: Mar. 3, 2020

(54) SYSTEM AND METHOD FOR A SYRINGE MICRO PUMP WITH WAVE SPRING

(71) Applicant: REPRO-MED SYSTEMS, INC., Chester, NY (US)

(72) Inventors: Andrew I Sealfon, Monroe, NY (US); Siavash Gheshmi, Rocklin, CA (US)

(73) Assignee: Repro-Med Systems, Inc., Chester, NY (US)

( * ) Notice: Subject to any disclaimer, the term of this patent is extended or adjusted under 35 U.S.C. 154(b) by 98 days.

(21) Appl. No.: 15/729,896

(22) Filed: Oct. 11, 2017

(65) Prior Publication Data

US 2018/0099086 A1   Apr. 12, 2018

Related U.S. Application Data

(60) Provisional application No. 62/407,376, filed on Oct. 12, 2016.

(51) Int. Cl.
*A61M 5/145*  (2006.01)
*A61M 5/168*  (2006.01)
(Continued)

(52) U.S. Cl.
CPC ........ *A61M 5/1454* (2013.01); *A61M 5/1456* (2013.01); *A61M 5/1458* (2013.01);
(Continued)

(58) Field of Classification Search
CPC ............ A61M 5/1454; A61M 5/14546; A61M 5/1456; A61M 2005/14573;
(Continued)

(56) References Cited

U.S. PATENT DOCUMENTS

| | | | |
|---|---|---|---|
| 4,959,056 A | | 9/1990 | Foshee et al. |
| 5,100,389 A | * | 3/1992 | Vaillancourt ....... A61M 5/1454 604/135 |

(Continued)

OTHER PUBLICATIONS

PCT International Search Report for International Application PCT/US2017/056170, search report dated Jan. 12, 2018 (Jan. 12, 2018).

*Primary Examiner* — Nilay J Shah
(74) *Attorney, Agent, or Firm* — Daniel W. Roberts; Law Offices of Daniel W. Roberts, LLC (57) ABSTRACT

Provided is a system and method for a removable syringe micro pump. The removable syringe micro pump includes a pump housing having a first end and opposite thereto an attaching end, and at least one sidewall there between, the housing having a base proximate to the first end and, the attaching end having an attacher structured and arranged to temporarily engage a syringe. At least one wave spring is nested within the housing and attached proximate to the base. The wave spring having has a compressed first position wherein the wave spring is disposed within the pump housing, and a second extended position wherein the release of tension extends the spring normally away from the pump housing. The wave spring has a diameter pre-selected to pass within a barrel of the engaged syringe. And engage a plunger seal of the syringe. An associated method of use is also provided.

38 Claims, 8 Drawing Sheets

(51) Int. Cl.
*A61M 5/162* (2006.01)
*F16F 1/04* (2006.01)
*A61M 5/31* (2006.01)

(52) U.S. Cl.
CPC ......... *A61M 5/168* (2013.01); *A61M 5/14546* (2013.01); *A61M 5/162* (2013.01); *A61M 5/3137* (2013.01); *A61M 2005/14573* (2013.01); *F16F 1/046* (2013.01)

(58) Field of Classification Search
CPC .................. A61M 5/1458; A61M 5/24; A61M 2005/2407; A61M 2005/2437; A61M 2005/2485; A61M 2005/2488; A61M 2005/2492; A61M 5/28; A61M 5/31565; A61M 5/31585; A61M 5/142; A61M 5/145; A61M 5/1452; A61M 5/3137; A61M 5/20; F16F 1/046
See application file for complete search history.

(56) References Cited

U.S. PATENT DOCUMENTS

| | | | |
|---|---|---|---|
| 5,383,858 A * | 1/1995 | Reilly | A61M 5/14546 604/131 |
| 5,656,034 A | 8/1997 | Kochersperger et al. | |
| 6,019,747 A * | 2/2000 | McPhee | A61M 5/1454 604/136 |
| 6,610,030 B1 | 8/2003 | Baxter | |
| 6,802,892 B2 | 10/2004 | Newman et al. | |
| 7,220,245 B2 * | 5/2007 | Kriesel | A61M 5/14244 604/134 |
| 8,945,063 B2 | 2/2015 | Wooton et al. | |
| 9,180,259 B2 | 11/2015 | Lesch, Jr. | |
| 2001/0056259 A1 | 12/2001 | Skinkel et al. | |
| 2011/0087173 A1 | 4/2011 | Sibbit et al. | |

* cited by examiner

SYSTEM AND METHOD FOR A SYRINGE MICRO PUMP WITH WAVE SPRING

CROSS REFERENCE TO RELATED APPLICATIONS

This application claims the benefit under 35 U.S.C. § 119(e) of U.S. Provisional Application No. 62/407,376 filed Oct. 12, 2016 and entitled SYSTEM AND METHOD FOR A SYRINGE MICRO PUMP WITH WAVE SPRING, the disclosure of which is incorporated herein by reference.

FIELD OF THE INVENTION

The present invention relates generally to syringe pumps as may be used to supply medication to a patient from a filled syringe via an infusion line. The pump acts to apply force to the plunger seal within the barrel of the syringe to move a solution from the syringe into the infusion line. By presetting the force applied by the pump to the plunger seal, the duration of time over which the solution will be infused may be managed. The compact nature of the pump permits its operation without concern for orientation, and without the risk of externally moving parts, such as the traditional syringe plunger binding and retarding the infusion.

BACKGROUND

Syringe pumps are commonly used for the infusion of a solution from a syringe through an infusion line to a patient. The infusion generally occurring slowly over a period of time.

The typical syringe consists of several well-known and understood components, not the least of which are a barrel between a nozzle and a set of finger grips, a plunger seal disposed within the barrel, and a plunger attached to the plunger seal and protruding from beyond the finger grips so as to permit an operator to draw the plunger seal away from the nozzle in a first instance—such as to draw a solution into the barrel of the syringe by way of the nozzle, and in a second instance to depress/drive the plunger seal towards the nozzle so as to dispense a solution from the barrel by way of the nozzle in a second instance.

It is therefore well understood and expected that the plunger is substantially about the same length as the barrel of the syringe. Moreover, when loaded with solution, the overall length of the syringe—i.e., the combined length of the barrel and plunger, may be about twice the length of the barrel alone.

As such, mechanical syringe pumps are traditionally at least as long as the extended plunger, so that they may accommodate the plunger and mechanically induce its progress from an initially extended state to a fully depressed and nested state.

Mechanical syringe pumps therefore inherently impose at least two issues that may be undesirable in some situations where the use of a syringe pump may be otherwise desired. The first is that by accommodating the range of motion of the plunger, the syringe pump adds significantly to the overall length of the syringe—generally at least the length of the syringe and the length of the plunger when fully retracted.

This added length thereby adds at least a second factor in that the length makes portage of the syringe and pump during use potentially undesirable and/or difficult. In addition, as the length of the housing is to accommodate the actuation of the plunger, a jarring of the syringe pump may harm the plunger and in turn impede the function of the syringe pump Moreover, the typical syringe pump cannot be unobtrusively placed in a coat pocket or pants pocket during use.

In addition, many syringe pumps are electrically powered, either by connection to an electrical grid or by batteries. In the first case, reliance upon an electrical grid makes the syringe pump less than easily portable during use where the patient may desire to leave the area of the grid connection. In the second case, storage of batteries requires extra space and weight for the syringe pump, which again may reduce the ease of portability.

Hence, there is a need for a method and system for a syringe pump that is capable of overcoming one or more of the above identified challenges.

SUMMARY OF THE INVENTION

Our invention solves the problems of the prior art by providing novel systems and methods for a removable syringe micro pump with wave spring.

In particular, and by way of example only, according to one embodiment of the present invention, provided is a system for a removable syringe micro pump with wave spring, including: a pump housing having a first end and opposite thereto an attaching end, and at least one sidewall there between, the housing having a base proximate to the first end and, the attaching end having an attacher structured and arranged to temporarily engage a syringe; at least one wave spring nested within the housing and attached proximate to the base, the wave spring having a first position wherein the wave spring is compressed under tension such that the initial height of the wave spring is disposed within the pump housing, the wave spring having a second extended position wherein, the release of tension extends the spring normally away from the pump housing, the wave spring having a diameter pre-selected to pass within a barrel of the engaged syringe, the wave spring further having a distal end structured and arranged to engage a plunder seal of the engaged syringe, wherein the release of tension between the first position and the second position permits the distal end of the wave spring to move the plunger seal towards a nozzle of the syringe.

For another embodiment, provided is a system for a removable syringe micro pump with wave spring, including: a cylindrical pump housing having a first end with a base and opposite thereto an attaching end providing at least one flange structured and arranged to temporarily bind with a set of finger grips provided by a syringe to which the cylindrical pump may be temporarily attached, the cylindrical pump having a central longitudinal axis; at least one wave spring disposed within the pump housing proximate to the base and about the longitudinal axis, the wave spring being axially compressible to fit within the cylindrical pump when a distal end of the wave spring is compressed to provide a first tensioned position, a height of the wave spring when compressed to the first tensioned position being about the same as a length of the cylindrical pump housing, the wave spring further selected to have a diameter sufficient to slide within a barrel of a syringe, the distal end of the wave spring structured and arranged to engage a plunger seal of the engaged syringe.

And for yet another embodiment, provided is a method for using a removable syringe micro pump with wave spring to dispense a solution from a syringe, including: providing a syringe having a barrel extending between a nozzle and a set of finger grips, a plunger seal disposed within the barrel and proximate to the finger grips, a solution disposed between the plunger seal and the nozzle; providing a removable syringe micro pump including: a cylindrical pump housing having a first end with a base and opposite thereto, an attaching end providing at least one flange structured and arranged to temporarily bind with the finger grips of the syringe, the cylindrical pump having a central longitudinal axis; a wave spring disposed within the cylindrical pump housing proximate to the base and about the longitudinal axis, the wave spring being compressible to fit within the cylindrical pump when a distal end of the wave spring is compressed to provide a first tensioned position, a height of the wave spring being about the same as a length of the cylindrical pump housing, the wave spring further selected to have a diameter sufficient to slide within the barrel of the syringe, the distal end of the wave spring structured and arranged to engage the plunger seal of the engaged syringe; and a wave spring restrainer structured and arranged to restrain the wave spring in the initial tension position until released by an operator; attaching the removable spring loaded micro pump to the syringe; and releasing the wave spring restrainer to permit the distal end of the wave spring to engage the plunger seal of the syringe, wherein, the release of tension from the first position permits the distal end of the wave spring to move the plunger seal towards the nozzle of the syringe, thereby, dispensing the solution from the syringe.

DETAILED DESCRIPTION

Before proceeding with the detailed description, it is to be appreciated that the present teaching is by way of example only, not by limitation. The concepts herein are not limited to use or application with a specific system or method for a removable syringe micro pump with wave spring. Thus, although the instrumentalities described herein are for the convenience of explanation shown and described with respect to exemplary embodiments, it will be understood and appreciated that the principles herein may be applied equally in other types of systems and methods involving micro pumps and specifically syringe micro pumps.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 first appears in FIG. 1.

Figure 1:
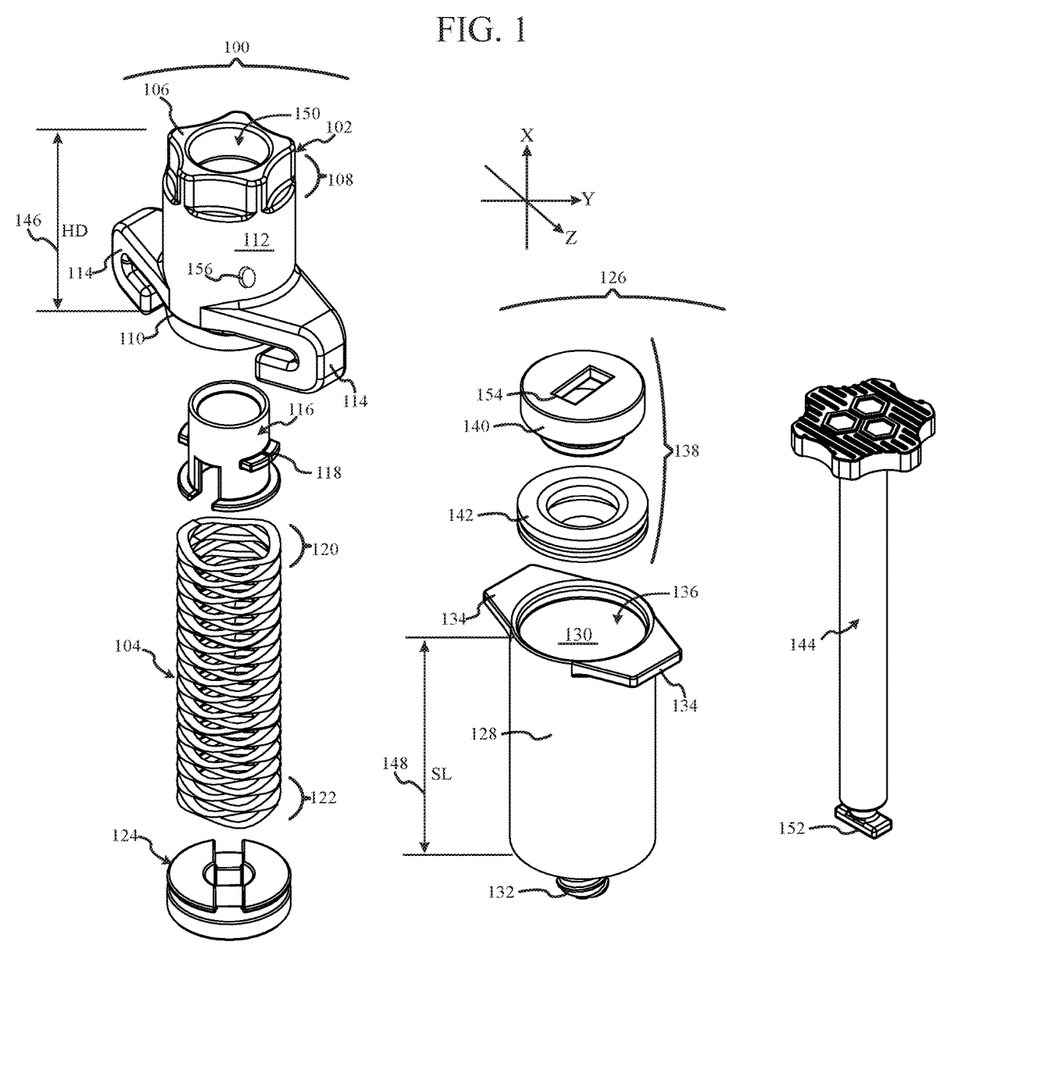
FIG. 1 is an exploded view of a removable syringe micro pump with wave spring in relation to a syringe and plunger in accordance with at least one embodiment.

Turning now to FIG. 1 there is shown an exemplary embodiment of a removable syringe micro pump 100, hereinafter RSMP 100 in exploded form. As shown, RSMP 100 is comprised principally of a pump housing 102 and a wave spring 104. As will be more fully appreciated by the description below, as RSMP 100 is removable, it may be provided separately to patients or parties desiring the use of a syringe micro pump, and may be reused by the same party or different parties and with the same syringe or different syringes.

To facilitate the description of systems and methods for this RSMP 100, the orientation of RSMP 100 as presented in the figures are referenced to the coordinate system with three axes orthogonal to one another as shown in FIG. 1. The axes intersect mutually at the origin of the coordinate system, which is chosen to be the center of the RSMP 100, however the axes shown in all figures are offset from their actual locations for clarity and ease of illustration.

The pump housing 102 provides a first end 106, which may in part be established by reinforcing base 108. Opposite from the first end 106 is an attaching end 110, and at least one sidewall 112 there between. For at least one embodiment, the attaching end 110 has a set of flanges 114. As is shown more completely in FIGS. 3A, 3B and 3C, for at least one embodiment the attaching end 110 further includes a seating collar which is seated in the open end of the syringe to assist with alignment when the RSMP 100 is attached to a syringe.

As shown, for at least one embodiment the pump housing 102 is cylindrical. Of course, for other embodiments, it may be desired to provide a pump housing 102 in a configuration having a square, hexagon, or geometric cross section other than a circle.

Within the pump housing 102 and proximate to the first end 106 is a spring mount 116 structured and arranged to receive and anchor the wave spring 104 to the pump housing 102. For at least one embodiment, the spring mount 116 has at least one mounting tab 118, structured and arranged to receive the wave spring 104.

As shown in FIG. 1 the wave spring 104 is in its extended/relaxed position. A wave spring is typically made from coiled flat wire with waves added to provide the spring effect. Wave springs can in general reduce spring height by 50% when compared to coil springs. As such they offer unique advantages of space savings. Moreover, the height of the compressed wave spring 104 when under tension is substantially less than the height of the wave spring 104 when extended.

Wave springs also produce a more consistent force across a range of deflections then traditional coil springs, which permit the RSMP 100 to be advantageously precise in terms of operation. In addition, unlike a traditional coil spring, a wave spring 104 does not develop torsional loads when compressed. As such wave spring 104 does not impart a rotation force during release of compression. Although typically used in applications requiring relatively short travel distances, wave spring 104 may be manufactured offering 50 mm of travel or more. And, for at least one embodiment, multiple wave springs may be employed in series.

Wave spring stiffness is determined by thickness and type of spring material as well as the number of waves per turn of the spring. As such, embodiments of RSMP 100 may be designed with different spring force characteristics so as to accommodate different liquids to be dispensed from the syringe For at least one embodiment, the first end 120, or proximal end, of the wave spring 104 is disposed about at least a portion of the spring mount 116 such that mounting tabs 118 engage the wave spring 104. As such, the distal end 122 of the wave spring 104 moves away from the spring mount 116 (and more specifically the reinforcing base 108) and the pump housing 102 as a whole, as tension in the wave spring 104 is released as the wave spring 104 transitions from a compressed first position to a relaxed/extended second position. For at least one embodiment, RSMP 100 includes an end driver 124, which receives at least a portion of the distal end 122 of the wave spring 104.

Adjacent to the RSMP 100 in FIG. 1 is a syringe 126, having a barrel 128 defining a chamber 130 between a nozzle 132 and a set of finger grips 134 adjacent to the open end 136 of the syringe 126. A plunger seal 138 is understood and appreciated to be the moveable element within the barrel 128, that may slide along the inside of the barrel 128 while maintaining a seal.

In some configurations, such as that shown, the plunger seal 138 may be comprised of a piston element 140 that is coupled to a seal element 142, generally comprised of a rubber, silicone, or other semi elastic material that may be used to provide the movable seal. For purposes of this discussion, the plunger seal 138 is understood to be this element, whether formed of one component or multiple components.

Also shown in FIG. 1 is the plunger 144 removed from the syringe 126 and disconnected from the plunger seal 138. When attached, the plunger 144 may be used by an operator engaging his or her fingers about the finger grips 134 to depress the plunger seal 138 from the location within the chamber 130 above the nozzle 132 towards the nozzle 132. The reverse is also true.

As may be appreciated in FIG. 1, the plunger 144 has an alignment specific attaching element 152, such as a rectangular flange. Likewise the plunger seal 138 has a corresponding mating attaching element 154, such as a rectangular receiver. As such, for at least one embodiment, the plunger 144 is engaged and disengaged from the plunger seal 138 by twisting when the plunger attaching element 152 is disposed within the plunger seal mating attaching element 154. For yet another embodiment, not shown, the plunger 144 has a push or pull mechanism that releases an attaching element coupling to the plunger seal 138.

When the plunger 144 is attached to the plunger seal 138, the operator may draw the plunger seal 138 away from the nozzle 132 towards the finger grips 134 by way of the plunger 144. This action creates a vacuum within the barrel 128 and permits the syringe 126 to draw up a fluid solution or gas through the nozzle 132 and thus substantially fill the barrel 128 between the nozzle 132 and the plunger seal 138.

With respect to FIG. 1, it is to be appreciated that as shown, the length of the plunger 144 is actually longer than the barrel 128 of the syringe 126. However, as the plunger 144 is removable, when the plunger seal 138 has been disposed adjacent to the finger grips 134, or at whatever other desired location within the barrel 128 is deemed appropriate, and the plunger 144 removed, the effective length of the syringe 126 is about that of the barrel 128 and nozzle 132.

Returning to the RSMP 100 and more specifically the attaching end 110 of the pump housing 102, it will be appreciated that the flanges 114 are structured and arranged to engage the finger grips 134 of the syringe 126. Moreover, when the pump housing 102 is disposed over the open end 136 of the syringe 126 adjacent to the finger grips 134, the operator rotates the components relative to one another, such that the finger grips 134 are engaged by the flanges 114. In much the same way the finger grips 134 provide a point of leverage for the fingers of a human operator; the finger grips 134 provide a point of leverage for the RSMP 100.

For at least one embodiment, the flanges 114 may be provided with an inset depression of substantially the size and shape of the finger grips 134, so that when rotated into place, the finger grips 134 are received by the depressions, and thereby locks the RSMP 100 in place. One or more additional springs, not shown, may provide a separation force as between the pump housing 102 and the syringe 126 to further engage the finger grips 134 with the flange recesses and ward against unintended separation of the RSMP 100 from the syringe 126.

It is also to be appreciated that the end driver 124 of the wave spring 104 is structured and arranged to engage the plunger seal 138 of the engaged syringe 126. In optional embodiments, the distal end 122 of the wave spring 104 may directly engage the plunger seal 138.

When the compressed wave spring 104 is released, the release of tension expands the wave spring 104 outward from the pump housing 102 and against the end driver 124 which in turn drives the plunger seal 138. As the pump housing 102 is locked in place against the finger grips 134 by the flanges 114, the expansion of the wave spring 104 from its compressed first position to the relaxed/extended second position drives the distal end 122 against the end driver 124 which correspondingly drives the and the plunger seal 138 towards the nozzle 132.

Moreover, it is to be understood and appreciated that the wave spring 104 is advantageously operating in place of the traditional plunger 144.

As is further shown in FIG. 1, the pump housing 102 has a dimension HD 146 along the sidewall 112. For at least one embodiment, this dimension HD 146 is less than the length of the syringe SL 148. For at least one embodiment, this dimension HD 146 may be about half the length SL 148. For at least one specific embodiment, this dimension HD 146 is less than half the length SL 148. Moreover, it is understood and appreciated that RSMP 100 is compact and does not substantially add to the overall length of the syringe 126 when attached.

More specifically, it should be understood and appreciated that the dimension of the sidewall 112 is less than the length of the syringe 126. For at least one embodiment, the dimension of the sidewall 112 of the pump housing 102 is less than half the length of the syringe 126. For at least one embodiment the dimension of the sidewall 112 of the pump housing 102 is less than one third of the length of the syringe 126. For at least one embodiment the dimension of the sidewall 112 of the pump housing 102 is less than one quarter of the length of the syringe 126. Moreover, it is understood and appreciated that RSMP 100 is compact and does not substantially add to the overall length of the syringe 126 when attached.

Further still, as the plunger 144 is removed, RSMP 100 coupled to syringe 126 may be disposed in a persons pocket, purse, pack or other space, and in generally any orientation during an infusion therapy session. As the motion of the wave spring 104 is entirely within the pump housing 102 and the barrel 128 of the syringe 126, it will not catch on, or be caught by, external items.

Although RSMP 100 is advantageously operational without the use of plunger 144, for at least one embodiment, RSMP 100, and more specifically the pump housing 102, provides a central aperture 150 such that the plunger 144 may pass directly through the RSMP 100 and engage the plunger seal 138. As such, plunger 144 may be used to reset RSMP 100 by using the plunger seal 138 to draw back the wave spring 104 to its compressed first position, ready for use to once again drive forward the plunger seal 138.

For at least one embodiment, RSMP 100 may further include a wave spring 104 restrainer 156 structured and arranged to restrain the wave spring 104 when it has been returned to the first position. For the exemplary embodiment shown in FIG. 1, an exemplary restrainer 156 is shown as a push button operating an internal lever coupling to a sliding pin engaging the edge of the wave spring 104 proximate to the distal end 122. The sliding pin may optionally engage a groove or slot in the side of the wave spring 104. Alternatively, a restrainer 156 may be an adjustable friction ring tightening about the wave spring 104. Of course it is understood and appreciated that a variety of mechanical elements may be employed as a restrainer 156 for the wave spring 104 within the teaching of this disclosure.

Figure 2A:
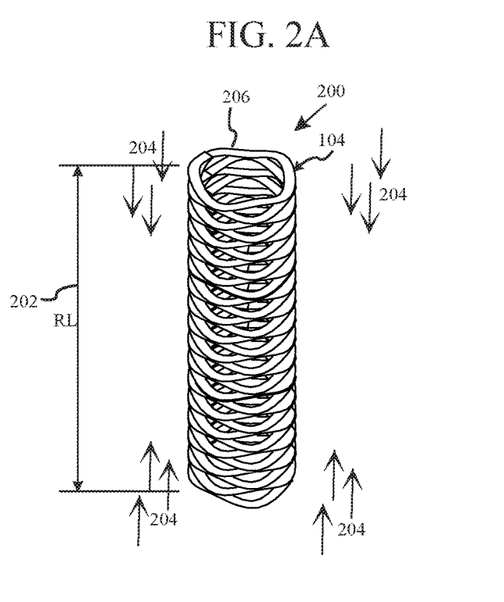
FIGS. 2A-2C are side and bottom views of the wave spring for the removable syringe micro pump with wave spring in accordance with at least one embodiment.
Figure 2B:
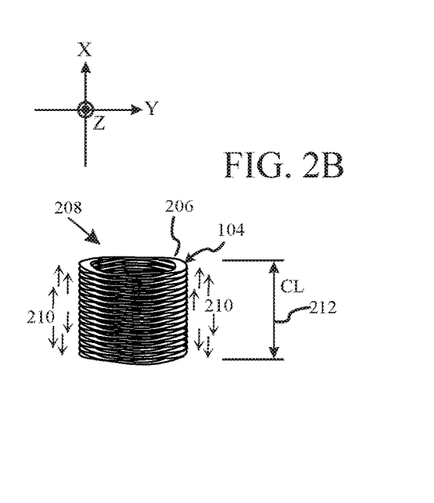
Figure 2C:
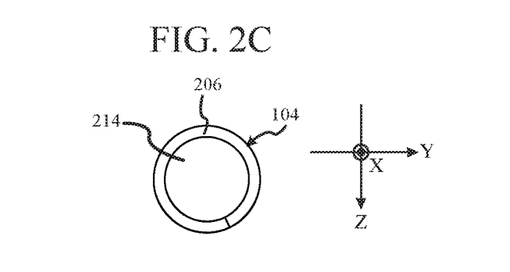

FIGS. 2A, 2B and 2C provide further illustrations to assist in understanding and appreciating the advantageous nature of the wave spring 104 as used in RSMP 100. More specifically, in FIG. 2A the wave spring 104 is shown in its relaxed/extended second position 200. In this second position 200 the wave spring has a relaxed length dimension RL 202.

By applying compressive force 204, the wave spring 104 is compressed such that the coils 206 stack vertically upon one another as the wave elements in each coil are compressed down, shown in FIG. 2B. This is the compressed first position 208 of the wave spring 104. In this state, the wave spring 104 is under tension as indicated by arrows 210. More specifically, the established tension force is an expansion force 210 which will drive the wave spring 104 back to it's relaxed/extended second position 200 once released from the compressed first position 208.

As may also be appreciated in FIG. 2B, in this first position 208 the wave spring has a compressed length dimension CL 212. As shown, the compressed length CL 212 is a fraction of the relaxed length dimension RL 202. It is also to be appreciated that the compressed length dimension CL 212 is less than the pump housing 102 dimension HD 146 (see FIG. 1), such that when wave spring 104 is in the first position 208 it may be disposed substantially within the pump housing 102.

As shown in FIG. 2C the nature of the coils 206 of the wave spring 104 is such that the wave spring has an open center 214. As such, this open center 214 permits the wave spring 104 to permit the plunger 144 to pass through the wave spring 104 and engage the plunger seal 138 when the plunger is disposed through the aperture 150 of the pump housing 102.

Further, for at least one embodiment the wave spring 104 is selected to have a tension correlated to dispense the solution from the syringe 126 over a pre-determined period of time. In other words, a first wave spring 104 with a first tension may be used to dispense a solution at a first rate while a second wave spring 104 with a second tension less than the first tension may be used to dispense the same solution at a second rate that is slower than the first rate.

For at least one embodiment, the wave spring 104 is selected to have a relaxed/extended second position 200 that is equal to or slightly in excess of the length of the barrel 128 so as to ensure that all of the solution within the barrel 128 of the syringe 126 is dispensed. It is also understood and appreciated that the wave spring 104 need not be compressed all the way back to first position 208 as shown.

Indeed, the wave spring 104 may be compressed so as to substantially return the majority of the wave spring 104 back to the pump housing 102 with the distal end 122 extending from the pump housing 102. Moreover the compressed first position 208 is understood and appreciated to be the initial position of wave spring 104 with respect to the pump housing 102 of RSMP 100 before the RSMP 100 is activated to drive the plunger seal 138 towards the nozzle 132.

Moreover, the wave spring 104 restrainer 156 permits the RSMP 100 to be attached to a syringe 126, but activation of the wave spring 104 is delayed until such time as infusion of the solution within the barrel 128 of the syringe 126 is desired.

Figure 3A:
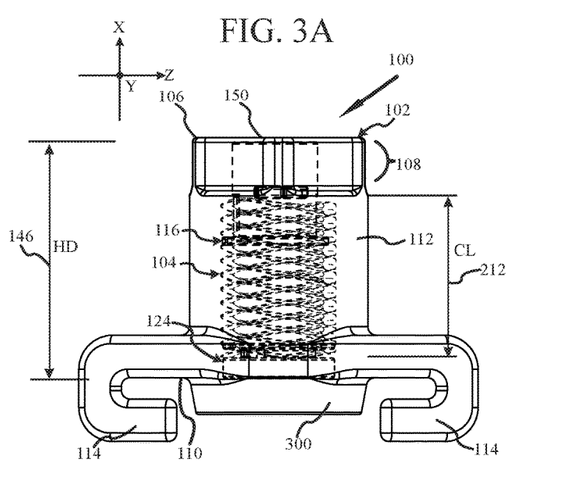
FIGS. 3A-3D are side, bottom and perspective views of the removable syringe micro pump with the wave spring enclosed therein in accordance with at least one embodiment.
Figure 3B:
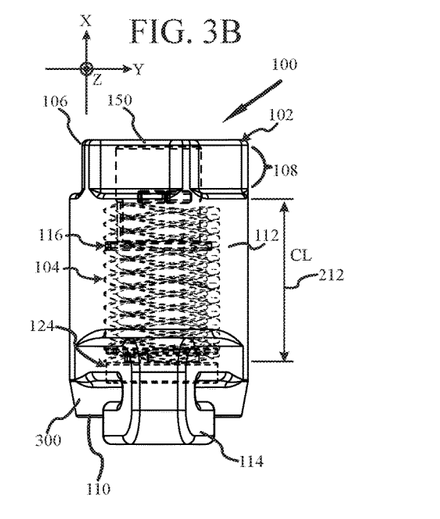
Figure 3C:
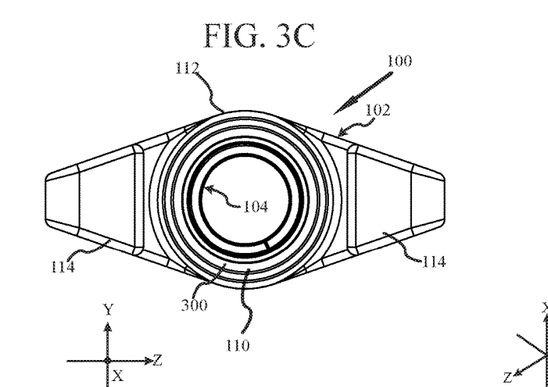
Figure 3D:
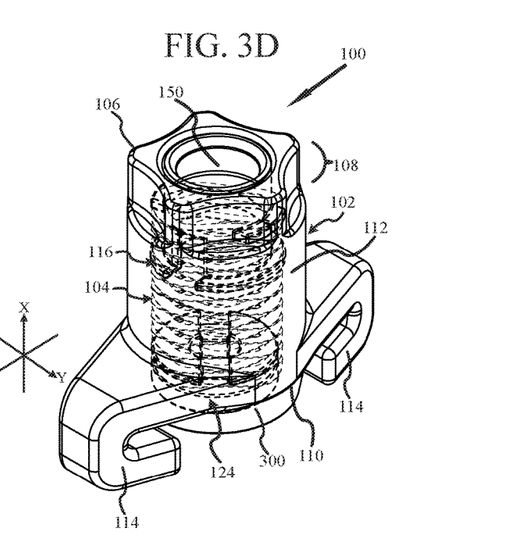

FIGS. 3A, 3B, 3C and 3D provide respectively front, side, bottom and perspective views of the RSMP 100. For each illustration as shown, the wave spring 104 has been shown in a compressed first position 208 within the pump housing 102. In FIG. 3A the compressed length dimension CL 212 of the wave spring 104 in relation to the height HD 146 of the pump housing 102 may also be more fully appreciated. Indeed, with respect to FIGS. 3A, 3B, 3C and 3D, the removable nature of RSMP 100 may be further appreciated, for the elements of RSMP 100 may be appreciated as comprising the distinct RSMP 100 without the presence of a syringe. As noted above, in FIGS. 3A-3D it may also be appreciated that for at least one embodiment, the attaching end 110 of RSMP 100 includes a seating base 300 that is structured and arranged to fit within the open end 136 of the barrel 128 of syringe 126 as is shown in FIGS. 4B, 5B, 6A and 6B.

To summarize, for at least one embodiment provided is an RSMP 100, including: a pump housing 102 having a first 106 end and opposite thereto an attaching end 110, and at least one sidewall 112 there between, the housing having a base 108 proximate to the first end 106 and, the attaching end 110 having an attacher 114 structured and arranged to temporarily engage a syringe 126; at least one wave spring 104 nested within the housing and attached proximate to the base 108, the wave spring 104 having a first position 208 wherein the wave spring 104 is compressed under tension such that the initial height of the wave spring 104 is disposed within the pump housing 102, the wave spring 104 having a second extended position 200 wherein, the release of tension extends the wave spring 104 normally away from the pump housing 102, the wave spring 104 having a diameter pre-selected to pass within a barrel 128 of the engaged syringe 126, the wave spring 104 further having a distal end 122 structured and arranged to engage a plunger seal 138 of the engaged syringe 126, wherein the release of tension between the first position 208 and the second position 200 permits the distal end 122 of the wave spring 104 to move the plunger seal 138 towards a nozzle 132 of the syringe 126.

Moreover, another embodiment may be summarized as an RSMP 100, including: a cylindrical pump housing 102 having a first end 106 with a base 108 and opposite thereto an attaching end 110 providing at least one flange 114 structured and arranged to temporarily bind with a set of finger grips 134 provided by a syringe 126 to which the cylindrical pump housing 102 may be temporarily attached, the cylindrical pump 100 having a central longitudinal axis; at least one wave spring 104 disposed within the pump housing 102 proximate to the base 108 and about the longitudinal axis, the wave spring 104 being axially compressible to fit within the cylindrical pump 102 when a distal end 122 of the wave spring 104 is compressed to provide a first tensioned position 208, a height 212 of the wave spring 104 when compressed to the first tensioned position 208 being about the same as a length of the cylindrical pump housing 102, the wave spring 104 further selected to have a diameter sufficient to slide within a barrel 128 of a syringe 126, the distal end 122 of the wave spring 104 structured and arranged to engage a plunger seal 138 of the engaged syringe 126.

Figure 4A:
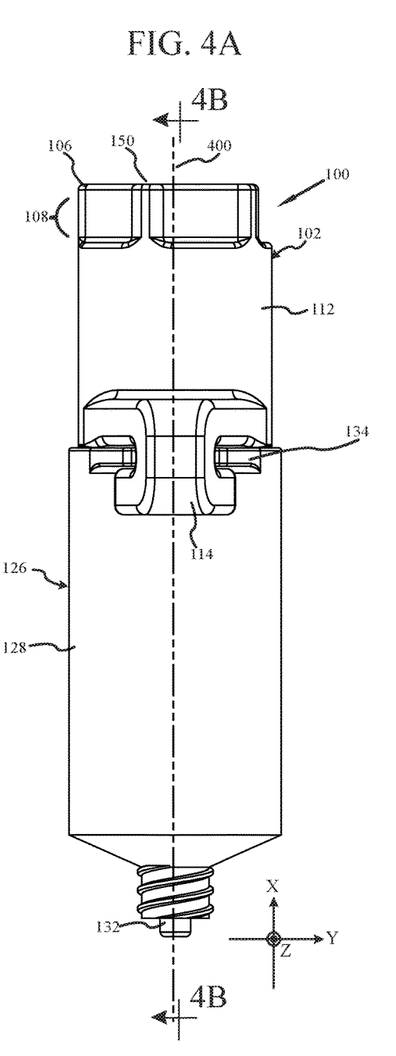
FIGS. 4A and 4B are side and cut through views of the removable syringe micro pump with wave spring as attached to a syringe with the wave spring in it's extended/relaxed position within the barrel of the syringe and the plunger seal driven towards the nozzle in accordance with at least one embodiment.
Figure 4B:
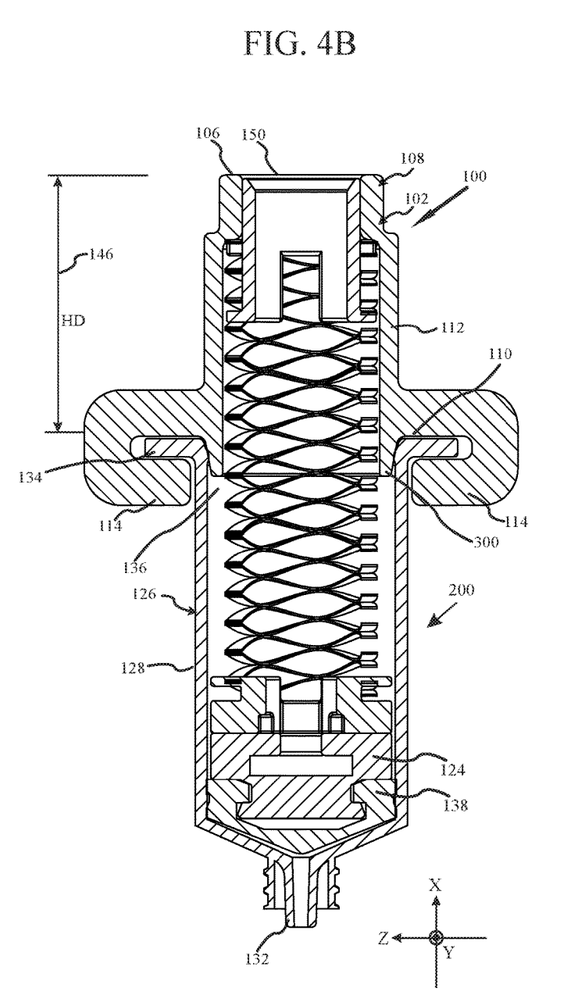

FIGS. 4A and 4B provide an assembled perspective view and corresponding cut through view of RSMP 100 engaged to syringe 126 in accordance with at least one embodiment. Moreover, in FIG. 4A the RSMP 100 has been disposed upon the syringe 126 such that the flanges 114 of the pump housing 102 have engaged the finger grips 134 of the syringe 126. With respect to FIG. 4A it is also to be appreciated that the overall length of the syringe 126 with RSMP 100 attached is only slightly longer then the length of the syringe 126 by itself.

Also, with respect to FIG. 4A being an external view, it is to be appreciated that the state of the wave spring 104 within the assembly of the RSMP 100 and syringe 126 need not be overtly apparent—especially if the barrel 128 of the syringe 126 is opaque.

In FIG. 4B, presenting the cut through view along longitudinal axis 400 and reference line arrows 4B in FIG. 4A, it can be seen that the wave spring 104 has expanded from its first compressed position within the pump housing 102 to a second relaxed position, and the exertion of force released during this change in positions has driven the plunger seal 138 down the length of the barrel 128 such that the plunger seal 138 is now proximate to the nozzle 132. The nature of the coupling of RSMP 100 to the barrel 128 of syringe 126 may also be more fully appreciated. As shown, the engaging end 110 of RSMP 100 abuts the open end 136 of the barrel 128 of syringe 126. For at least one embodiment, the seating collar 300 is disposed within the open end 136, and facilitates proper alignment during attachment of RSMP 100 to the syringe 126. Moreover, it is to be understood and appreciated that the syringe remains external to the sidewall 112 of the pump housing 102.

Figures 5A, 5B:
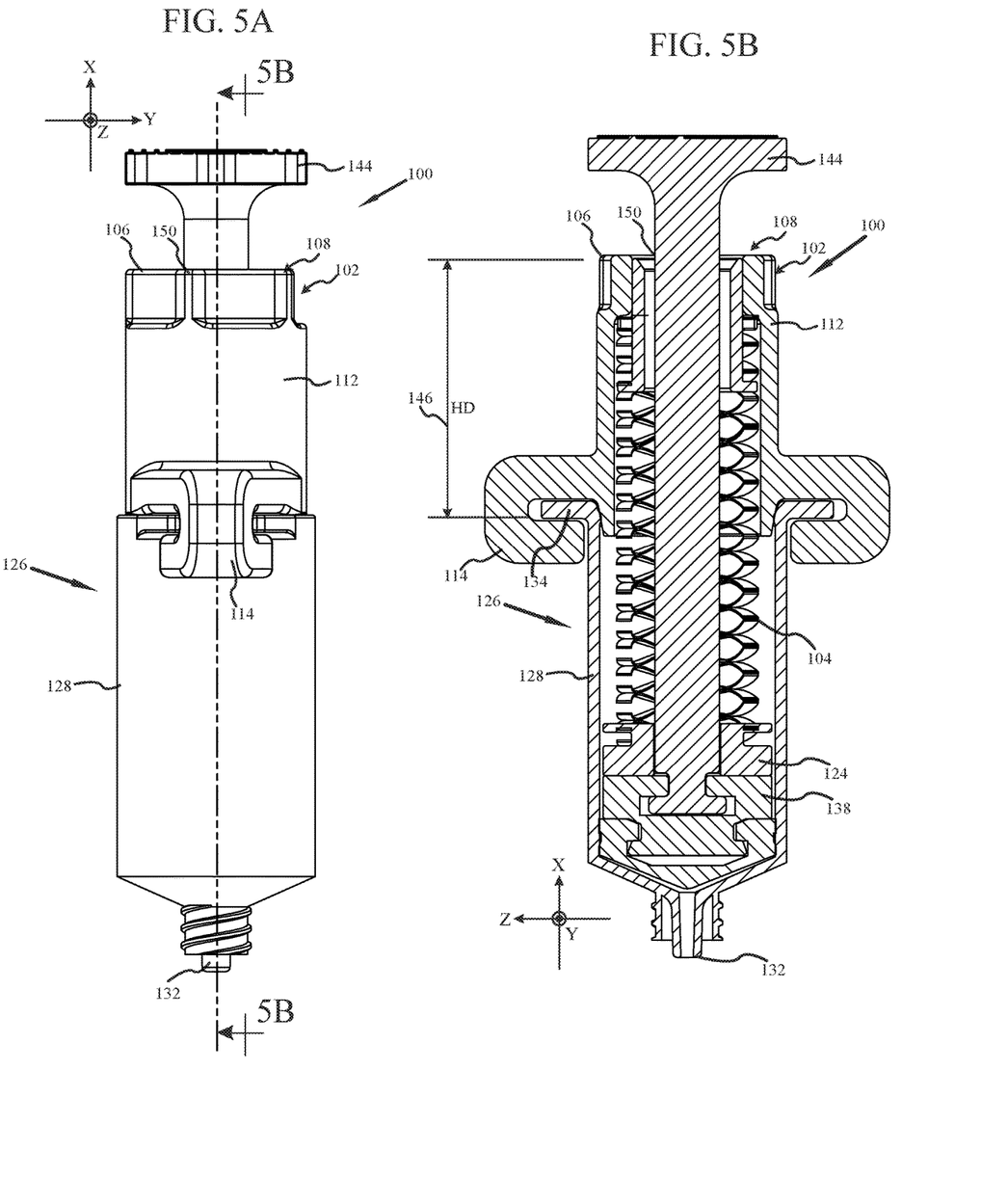
FIGS. 5A and 5B are side and cut through views of the removable syringe micro pump with wave spring as attached to a syringe with the wave spring in it's extended/relaxed position within the barrel of the syringe and the plunger seal driven towards the nozzle and the plunger inserted to reset the removable syringe micro pump in accordance with at least one embodiment.

FIGS. 5A and 5B provide similar assembled perspective view (FIG. 5A) and corresponding cut through view (FIG. 5B along reference line arrows 5B in FIG. 5A) of RSMP 100 engaged to syringe 126, and this time further showing the plunger 144 as disposed through the aperture 150 of the pump housing 102 in accordance with at least one embodiment. As noted above, it is understood and appreciated that during typical use of the RSMP 100 the plunger will be removed so as to minimize the overall space required for operation, as well as to eliminate the opportunity for the plunger to become bound or otherwise restrained by some foreign object, which would in turn frustrate the operation of RSMP 100.

As shown in FIGS. 5A and 5B, the plunger 144 may be disposed through RSMP 100 so as to engage the plunger seal 138 and draw it back from the nozzle 132 towards the finger grips 134. As such, the plunger 144 may be used to reset RSMP 100 by returning the wave spring to it's compressed first position 208. In addition, as with a traditional syringe, drawing the plunger 144 back creates a vacuum within the chamber of the syringe 126 such that a fluid may be drawn into the syringe 126 from a source reservoir. Moreover, the plunger 144 may be employed to both prime the syringe 126 as well as reset the RSMP 100.

FIGS. 6A and 6B, and 7A and 7B provide side cut through views illustrating the RSMP 100 in use. More specifically, FIG. 6A corresponds to the initial state of RSMP 100 when attached to syringe 126 with plunger seal 138 disposed adjacent to the finger grips 134. In actual use a fluid or medication, represented by dots 600, such as for an infusion therapy, would be present within the chamber 130 between the plunger seal 138 and the nozzle 132.

Figure 6A:
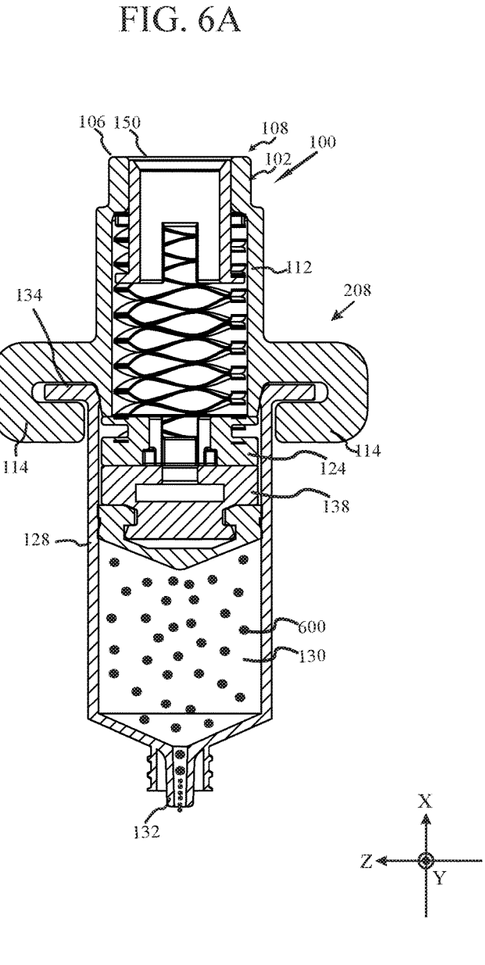
FIGS. 6A, 6B and 7A and 7B are side cut through views showing the removable syringe micro pump with wave spring in operation, driving the plunger seal towards the nozzle of the syringe in accordance with at least one embodiment of the present invention.
Figure 6B:
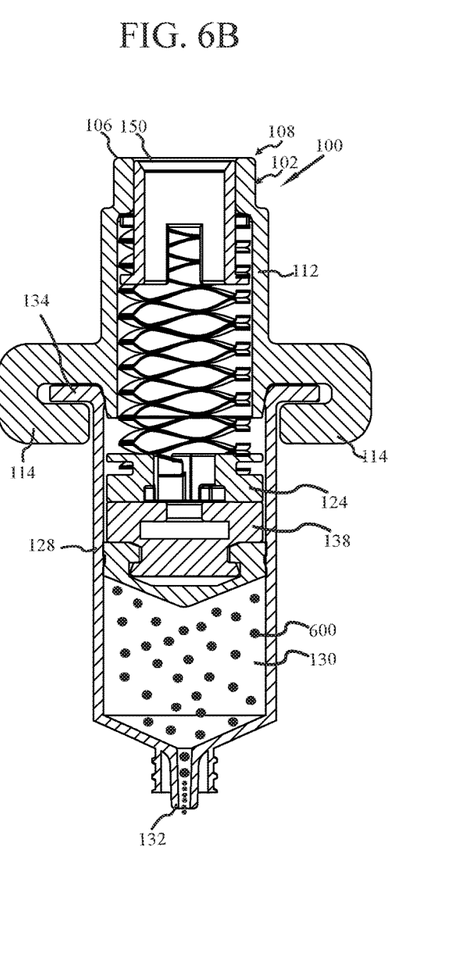

In FIG. 6B the RSMP 100 has been activated such that wave spring 104 has been released from it's compressed/tensioned first position 208 and has engaged the plunger seal 138 by way of the end driver 124 to move it approximately one-third of the way along the barrel 128 towards the nozzle 132, thus dispensing the fluid 600. In actual use, the syringe 126, and more specifically the nozzle 132 would be coupled to tubing or other delivery conduit, which has not been shown so as to simplify the illustration.

Figure 7A:
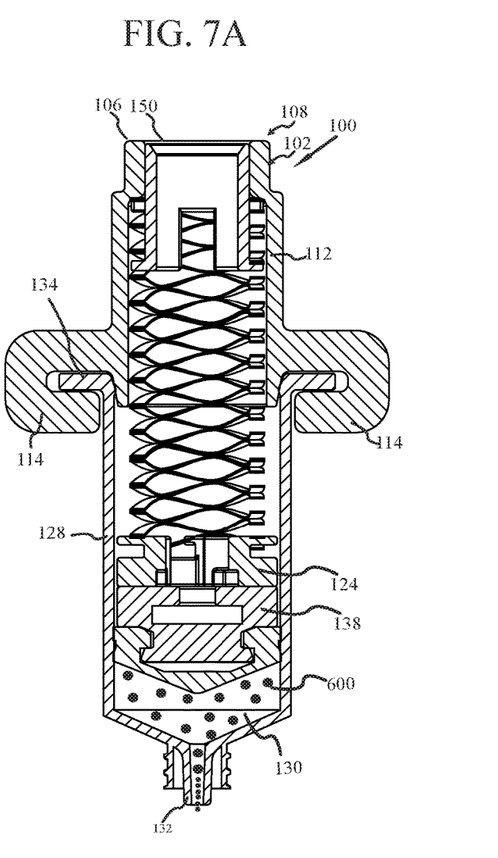

In FIG. 7A the RSMP 100 has continued in operation such that the wave spring 104 has now driven the plunger seal 138 approximately two-thirds of the way along the barrel 128 towards the nozzle 132, thus further dispensing the fluid 600.

Figure 7B:
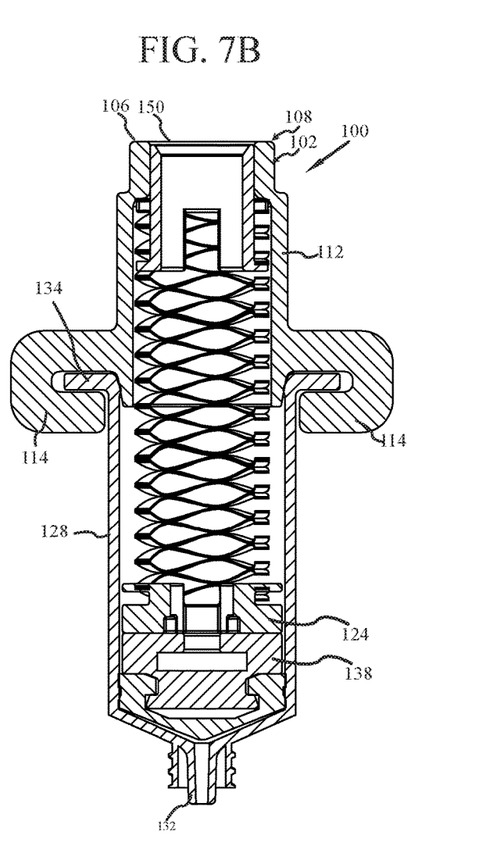

And in FIG. 7B the RSMP 100 has ceased operation as the wave spring 104 has now driven the plunger seal 138 substantially to the end of the barrel 128 such that substantially all of the fluid has now been dispensed from the syringe 126.

Moreover, with respect to FIGS. 6A, 6B, 7A, 7B the expansion of the wave spring 104 and thus the progression of the plunger seal 138, will continue until the either the wave spring 104 has reached its extended/relaxed second position, the plunger seal 138 has encountered the end of the barrel 128, or a restraining mechanism (not shown) is engaged to prevent further expansion of the wave spring 104. For at least one embodiment, the wave spring 104 is selected to have a fully extended state that is equal to or slightly in excess of the length of the barrel 128 so as to ensure that all of the solution within the barrel 128 of the syringe 126 is dispensed.

Further, as evidenced especially in FIGS. 6A, 6B, 7A, 7B, the motion of the wave spring 104 occurs entirely within the RSMP 100 and the barrel 128 of the syringe 126. Moreover, there is no external change in the dimension of the coupled RSMP 100 and syringe 126 during operation, e.g., no plunger 144 to be caught or interfered with. It should also be noted that although exemplary FIGS. 6A, 6B, 7A, 7B have demonstrated the use of RSMP 100 to drive the plunger seal 138 from a starting point proximate to the finger grips 134 to the end of the barrel 128 proximate to the nozzle 132, e.g., a full syringe, it is to be understood and appreciated that RSMP 100 is equally applicable and appropriate for use with a syringe having an initial starting volume that is less than an otherwise full syringe.

This small compact nature of the RSMP 100 and syringe 126 may facilitate infusion while the combined structure is disposed within a pocket. Further, as the operation of the wave spring 104 is a mechanical release of tension, it will be understood and appreciated that operation of the RSMP 100 is independent of orientation.

For shipping and transport, the RSMP 100 may be attached to the syringe 126 barrel 128 and the plunger 144 inserted through the aperture 150 of the pump housing 102 and seated with plunger seal 138, which in turn is disposed against the bottom of the syringe 126 adjacent to the nozzle 132. The syringe 126 and RSMP 100 are therefore a compact system. When use of the RSMP 100 is desired, the plunger 144 may be withdrawn so as to pull back the plunger seal 138, and in the process fill the barrel 128 with a desired solution for subsequent infusion.

With the plunger seal 138 properly disposed at a point, sufficient to provide a desired amount of solution, the plunger 144 may be disengaged from the plunger seal 138 and discarded. With the plunger 144 now removed, the RSMP 100 and syringe 126 are once again an advantageously compact system. As before, operation of the wave spring 104 is entirely internal, such that there is no external change in size.

With respect to the above description of RSMP 100, the removable nature of RSMP 100 noted above may now be more fully appreciated. Indeed, the RSMP 100 is not just removable, but also reusable. Thus RSMP 100 may be reset and attached to new syringes, which have been primed and delivered without a syringe pump thus permitting a savings across a spectrum of categories including but not limited to shipping, storage, materials and education of use. Once a patient or party is finished with RSMP 100, the RSMP 100 may also be recycled back to a new party. Further still, an RSMP 100 may be shared by multiple parties, obviously using RSMP 100 at different times.

Figure 8:
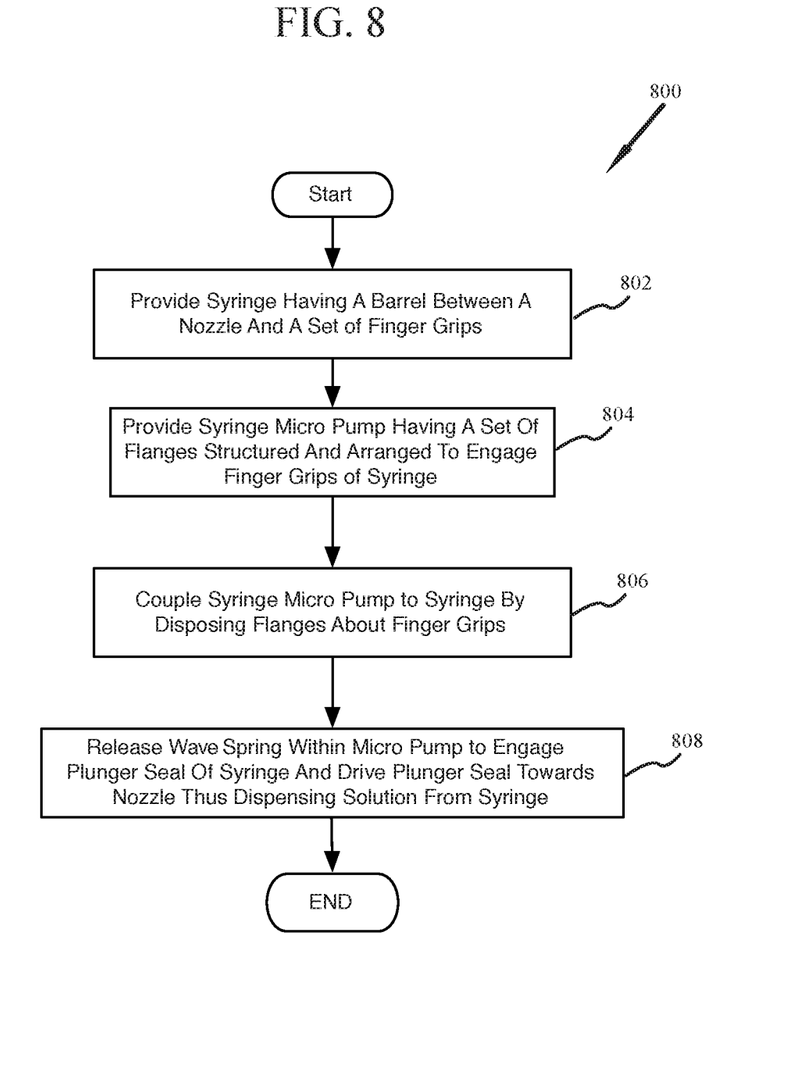
FIG. 8 is a flow diagram presenting a high level review of at least one method for using a removable syringe micro pump with wave spring in accordance with at least one embodiment of the present invention.

Having described embodiments for the RSMP 100, other embodiments relating to at least one method 800 of using the RSMP 100 will now be discussed with respect to the above illustration and specifically FIG. 8. It will be appreciated that the described method 700 need not be performed in the order in which it is herein described, but that this is merely exemplary of one method for using RSMP 100.

In general, the method 800 of use commences with providing a syringe 126 having a barrel 128 extending between a nozzle 132 and a set of finger grips 134, block 802. For simplicity, it will be assumed that a plunger seal 138 is disposed within the barrel 128 and proximate to the finger grips 134 with a solution disposed between the plunger seal 138 and the nozzle 132. Moreover, this is a syringe 126 in a ready state for use to provide a solution for infusion to a patient.

The RSMP 100 having a set of flanges 114 structured and arranged to engage the finger grips 134 is then provided, block 804. Moreover, the RSMP 100 provided is as described above, comprised principally of a pump housing 102 and a wave spring 104. Method 800 continues with the coupling of RSMP 100 to the syringe 126 by disposing the flanges 114 about the finger grips 134, block 806.

The wave spring 104 is then released to engage the plunger seal 138 of the syringe 126 and drive the plunger seal 138 towards the nozzle 132, thus dispensing the solution from the syringe 126, block 808.

With respect to the above description regarding RSMP 100 and the associated method 700 of use, for at least one embodiment the wave spring 104 may be sheathed by at least one volute spring, not shown. More specifically, one or more volute springs may be used, at least in part, to protect the wave spring and help ensure that it does not buckle during compression or expansion. For yet another embodiment, the wave spring 104 may be combined with a volute spring in an ordered alignment to cooperatively interact and drive the plunger seal 138 of the syringe 126 towards the nozzle 132. Moreover, whether acting at least in part as a sheath about the wave spring 104 or as additional spring elements in alignment with the wave spring 104, the one or more volute springs may be used in the removable micro pump set for and described in U.S. patent application Ser. No. 15/291,758 filed Oct. 12, 2016 and entitled System and Method for a Removable Syringe Micro Pump With Volute Spring, now U.S. Pat. No. 10,406,282, the disclosure of which is incorporated herein by reference.

Changes may be made in the above methods, systems and structures without departing from the scope hereof. It should thus be noted, that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A system for a removable syringe micro pump with at least one wave spring, comprising:
   a pump housing having a first end and opposite thereto an attaching end, and at least one sidewall there between, the pump housing having a base proximate to the first end and, the attaching end having an attacher structured and arranged to temporarily engage a syringe having a barrel with an open end opposite from a nozzle, the attacher structured and arranged to attach to the open end of the syringe, the syringe remaining external to the sidewall of the pump housing;
   the at least one wave spring nested within the pump housing and attached proximate to the base, the at least one wave spring having a first position wherein the at least one wave spring is compressed under tension such that an initial height of the at least one wave spring is disposed within the pump housing, the at least one wave spring having a second extended position wherein, the release of the tension extends the at least one wave spring normally away from the pump housing, the at least one wave spring having a diameter pre-selected to pass within a barrel of the engaged syringe, the at least one wave spring further having a distal end structured and arranged to engage a plunger seal of the engaged syringe, wherein the release of the tension between the first position and the second position permits the distal end of the at least one wave spring to move the plunger seal towards the nozzle of the syringe.

2. The system for the removable syringe micro pump of claim 1, wherein the syringe has a set of finger grips, the attacher being a set of opposing flanges structured and arranged to engage the finger grips.

3. The system for the removable syringe micro pump of claim 1, further including an end driver receiving at least a portion of the distal end of the at least one wave spring, the end driver engaging the plunger seal.

4. The system for the removable syringe micro pump of claim 1, wherein the sidewall of the pump housing has a length dimension slightly larger than the height of the at least one wave spring in the first position.

5. The system for the removable syringe micro pump of claim 4, wherein the syringe has a length, the length dimension of the sidewall being less than half the length of the syringe.

6. The system for the removable syringe micro pump of claim 1, wherein the syringe has a removable plunger initially coupled to the plunger seal, the plunger activated to draw the plunger seal to an end of the syringe opposite from the nozzle, the plunger removed prior to the attachment of the pump housing with the at least one wave spring in an initial position to the syringe.

7. The system for the removable syringe micro pump of claim 1, wherein the pump housing has a central aperture in the base structured and arranged to receive a plunger when the pump housing is attached to the syringe.

8. The system for the removable syringe micro pump of claim 1, wherein operation of the removable syringe micro pump as attached to the syringe is unaffected by orientation.

9. The system for the removable syringe micro pump of claim 1, wherein the tension of the at least one wave spring is selected to dispense a solution from the syringe over about a pre-determined period of time.

10. The system for the removable syringe micro pump of claim 1, wherein removing the pump housing from the syringe disengages the at least one wave spring from the plunger seal and halts progression of the plunger seal towards the nozzle of the syringe.

11. The system for the removable syringe micro pump of claim 1, wherein the removable syringe micro pump is reusable.

12. The system for the removable syringe micro pump of claim 1, wherein during operation of the removable syringe micro pump when coupled to the syringe, motion of the at least one wave spring occurs entirely within the pump housing and the barrel of the syringe.

13. The system for the removable syringe micro pump of claim 1, wherein the sidewall of the pump housing is cylindrical.

14. The system for the removable syringe micro pump of claim 1, further including at least one volute spring at least partially disposed about the at least one wave spring.

15. The system for the removable syringe micro pump of claim 1, further including at least one volute spring in axial alignment with the at least one wave spring.

16. A system for a removable syringe micro pump with at least one wave spring, comprising:
  a cylindrical pump housing having a first end with a base and opposite thereto an attaching end providing at least one flange structured and arranged to temporarily bind with a set of finger grips provided by a syringe to which the cylindrical pump housing may be temporarily attached, the syringe having an open end opposite from a nozzle, the attaching end abutting the open end of the syringe, the cylindrical pump housing having a central longitudinal axis;
  the at least one wave spring disposed within the cylindrical pump housing proximate to the base and about the longitudinal axis, the at least one wave spring being axially compressible to fit within the cylindrical pump housing when a distal end of the at least one wave spring is compressed to provide a first tensioned position, a height of the at least one wave spring when compressed to the first tensioned position being about the same as a length of the cylindrical pump housing, the at least one wave spring further selected to have a diameter sufficient to slide within a barrel of the syringe, the distal end of the at least one wave spring structured and arranged to engage a plunger seal of the engaged syringe.

17. The system for the removable syringe micro pump of claim 16, wherein, the length of the cylindrical pump housing has a length dimension slightly larger than the height of the at least one wave spring in the first tensioned position.

18. The system for the removable syringe micro pump of claim 16, further including an end driver receiving at least a portion of the distal end of the at least one wave spring, the end driver engaging the plunger seal.

19. The system for the removable syringe micro pump of claim 16, wherein the syringe has a length, the length of the cylindrical pump housing being less than half the length of the syringe.

20. The system for the removable syringe micro pump of claim 16, wherein the cylindrical pump housing has a central aperture in the base structured and arranged to receive a plunger when the pump housing is attached to the syringe.

21. The system for the removable syringe micro pump of claim 16, wherein the cylindrical pump housing further includes a wave spring restrainer operable to hold the at least one wave spring in the first tensioned position until an operator desires to release the at least one wave spring to a second extended position.

22. The system for the removable syringe micro pump of claim 16, wherein operation of the removable syringe micro pump as attached to the syringe is unaffected by orientation.

23. The system for the removable syringe micro pump of claim 16, wherein the at least one wave spring is selected to have a tension correlated to dispense a solution from the syringe over about a pre-determined period of time.

24. The system for the removable syringe micro pump of claim 16, wherein removing the cylindrical pump housing from the syringe disengages the at least one wave spring from the plunger seal and halts progression of the plunger seal towards the nozzle of the syringe.

25. The system for the removable syringe micro pump of claim 16, wherein the removable syringe micro pump is reusable.

26. The system for the removable syringe micro pump of claim 16, wherein during operation of the removable syringe micro pump when coupled to for the removable syringe, motion of the at least one wave spring occurs entirely within the cylindrical pump housing and the barrel of the syringe.

27. The system for the removable syringe micro pump of claim 16, wherein including at least one volute spring at least partially disposed about the at least one wave spring.

28. The system for the removable syringe micro pump of claim 16, wherein including at least one volute spring in axial alignment with the at least one wave spring.

29. A method for using a removable syringe micro pump with at least one wave spring to dispense a solution from a syringe, comprising:
  providing the syringe having a barrel extending between a nozzle and a set of finger grips, a plunger seal disposed within the barrel and proximate to the finger grips, the solution disposed between the plunger seal and the nozzle;
  providing a removable syringe micro pump including:
    a cylindrical pump housing having a first end with a base and opposite thereto an attaching end providing at least one flange structured and arranged to temporarily bind with the finger grips of the syringe, the syringe having an open end opposite from the nozzle, the attaching end abutting the open end of the syringe, the cylindrical pump housing having a central longitudinal axis;

the at least one wave spring disposed within the cylindrical pump housing proximate to the base and about the longitudinal axis, the at least one wave spring being compressible to fit within the cylindrical pump housing when a distal end of the at least one wave spring is compressed to provide a first position, a height of the at least one wave spring being about the same as a length of the cylindrical pump housing, the at least one wave spring further selected to have a diameter sufficient to slide within the barrel of the syringe, the distal end of the at least one wave spring structured and arranged to engage the plunger seal of the engaged syringe; and a wave spring restrainer structured and arranged to restrain the at least one wave spring in the first position until released by an operator;

attaching the removable spring loaded micro pump to the syringe; and releasing the at least one wave spring restrainer to permit the distal end of the at least one wave spring to engage the plunger seal of the syringe, wherein, the release of tension from the first position permits the distal end of the wave spring to move the plunger seal towards the nozzle of the syringe, thereby, dispensing the solution from the syringe.

30. The method of claim 29, wherein the length of the cylindrical pump housing has a length dimension slightly larger than the height of a coil of the wave spring in the first position.

31. The method of claim 29, wherein the removable syringe micro pump further includes an end driver receiving at least a portion of the distal end of the at least one wave spring, the end driver engaging the plunger seal.

32. The method of claim 29, wherein the syringe has a length, the length of the cylindrical pump housing being less than half the length of the syringe.

33. The method of claim 29, wherein the cylindrical pump housing has a central aperture in the base structured and arranged to receive a plunger when the cylindrical pump housing is attached to the syringe.

34. The method of claim 29, wherein operation of the removable syringe micro pump as attached to the syringe is unaffected by orientation.

35. The method of claim 29, wherein the at least one wave spring is selected to have a tension correlated to dispense the solution from the syringe over about a pre-determined period of time.

36. The method of claim 29, wherein removing the cylindrical pump housing from the syringe disengages the at least one wave spring from the plunger seal and halts progression of the plunger seal towards the nozzle of the syringe.

37. The method of claim 29, wherein the removable syringe micro pump is reusable.

38. The method of claim 29, wherein during operation of the removable syringe micro pump when coupled to the syringe, motion of the at least one wave spring occurs entirely within the pump housing and the barrel of the syringe.

* * * * *